US00RE48864E

(19) United States
(12) Reissued Patent
Leist et al.

(10) Patent Number: US RE48,864 E
(45) Date of Reissued Patent: Dec. 28, 2021

(54) CELL CULTURE MEDIUM

(71) Applicant: NOVARTIS AG, Basel (CH)

(72) Inventors: Christian Leist, Gipf-Oberfrick (CH); Petra Meissner, Laufenburg (CH); Jörg Schmidt, Weil am Rhein (DE)

(73) Assignee: Novartis AG, Basel (CH)

(21) Appl. No.: 16/114,731

(22) Filed: Aug. 28, 2018

Related U.S. Patent Documents

Reissue of:
(64) Patent No.: 9,428,727
Issued: Aug. 30, 2016
Appl. No.: 13/643,998
PCT Filed: Apr. 25, 2011
PCT No.: PCT/EP2011/056508
§ 371 (c)(1),
(2) Date: Jan. 7, 2013
PCT Pub. No.: WO2011/134920
PCT Pub. Date: Nov. 3, 2011

U.S. Applications:
(60) Provisional application No. 61/327,836, filed on Apr. 26, 2010.

(51) Int. Cl.

| | |
|---|---|
| ***C12N 5/02*** | (2006.01) |
| ***C12N 5/00*** | (2006.01) |
| ***C12N 5/07*** | (2010.01) |
| ***C12N 5/071*** | (2010.01) |
| ***C12N 5/10*** | (2006.01) |
| ***C12P 21/04*** | (2006.01) |
| ***C12P 21/06*** | (2006.01) |

(52) U.S. Cl.
CPC ..... *C12N 5/005* (2013.01); *C12N 5/0018* (2013.01); *C12N 2500/05* (2013.01); *C12N 2500/12* (2013.01)

(58) Field of Classification Search
CPC ..... C12N 5/005; C12N 2500/12
See application file for complete search history.

(56) References Cited

U.S. PATENT DOCUMENTS

| | | | | |
|---|---|---|---|---|
| 5,135,866 | A | 8/1992 | Heifetz et al. | |
| 5,232,848 | A | 8/1993 | Wolfe et al. | |
| 5,672,502 | A | 9/1997 | Birch et al. | |
| 5,856,179 | A | 1/1999 | Chen et al. | |
| 5,871,999 | A | 2/1999 | Boraston | |
| 6,048,728 | A * | 4/2000 | Inlow et al. | 435/404 |
| 6,406,909 | B1 | 6/2002 | Shibuya et al. | |
| 7,294,484 | B2 * | 11/2007 | Drapeau et al. | 435/69.1 |
| 8,034,617 | B2 | 10/2011 | Aerts et al. | |
| 8,198,084 | B2 | 6/2012 | Gorfien et al. | |
| 2005/0019859 | A1 | 1/2005 | Schilling et al. | |
| 2006/0148074 | A1 | 7/2006 | Gorfien et al. | |
| 2007/0190057 | A1 | 8/2007 | Wu et al. | |
| 2007/0231895 | A1 | 10/2007 | Lee et al. | |
| 2008/0076155 | A1 | 3/2008 | Fung | |
| 2008/0108553 | A1 * | 5/2008 | Luan et al. | 514/2 |
| 2009/0088370 | A1 | 4/2009 | Winge | |

FOREIGN PATENT DOCUMENTS

| | | | |
|---|---|---|---|
| EP | 0283942 | A2 | 9/1988 |
| EP | 1757700 | A2 | 2/2007 |
| WO | 199808934 | | 3/1998 |
| WO | 2000/073431 | A2 | 12/2000 |
| WO | 0073431 | A2 | 12/2000 |
| WO | 02101019 | A2 | 12/2002 |
| WO | 20050019859 | A2 | 3/2005 |
| WO | 2006/026408 | A2 | 3/2006 |
| WO | 2006/026445 | A1 | 3/2006 |
| WO | 2006/113629 | A1 | 10/2006 |
| WO | 2011134920 | | 11/2011 |

OTHER PUBLICATIONS

Waymouth, "Osmolality of Mammalian Blood and of Media for Culture of Mammalian Cells", In Vitro, vol. 6(2), pp. 109-127 (1970).
Ham et al, "Media and Growth Requirements", LVIII Methods in Enzymology, pp. 44-93 (1979).
Takahashi et al, "Role of sodium and potassium ions in regulation of glucose metabolism in cultured astroglia", Proceedings of the National Academy of Sciences USA, vol. 92, pp. 4616-4620 (1995).
Sinicore et al, "Adaption of Mammalian Ceils to Growth in Serum-Free Media", Molecular Biotechnology, vol. 15, pp. 249-257 (2000).
Scott et al, "Effect of choline, high potassium, and low sodium on the number of neurons in cultures of dissociated chick ganglia", Experimental Neurology, vol. 31(2), pp. 183-188 (1971).
Trummer et al, "Process parameter shifting: Part II. Biphasic cultivation—A tool for enhancing the volumetric productivity . . . ", Biotech. & Bioengineering, vol. 94, No. 6, pp. 1045-1052 (2006).
Yoon, S.K. et al, "Biphasic culture strategy for enhancing volumetric erythropoietin productivity of Chinese hamster ovary cells"; Enzyme & Microbial Tech., vol. 39, No. 3, pp. 362-365 (2006).
Preliminary amendment of application U.S. Appl. No. 11/151,647, filed May 11, 2007.
Internet Website, Encyclopedia of Industrial Biotechnology: Bioprocess, Bioseparation, and Cell Technology, 7 Volume Set (Apr. 12, 2010).
Press release of Encyclopedia of Industrial Biotechnology: Bioprocess, Bioseparation, and Ceil Technology, 7 Volume Set (Apr. 12, 2010).
Letter as filed with the USPTO on May 11, 2007 in connection with US 2006/0148074.
Letter as filed with the USPTO on Apr. 4, 2016 in connection with the US examination proceedings of the U.S. Appl. No. 13/643,998.
Sørensen et al, "Purification and characterization of three proteins isolated from the proteose peptone fraction of bovine milk", Journal of Dairy Research, vol. 60, pp. 189-197 (1993).

(Continued)

*Primary Examiner* — Bruce R Campell
(74) *Attorney, Agent, or Firm* — Nelson Mullins Riley & Scarborough LLP; Jane E. Remillard, Esq.; Jill Gorny Sloper, Esq.

(57) ABSTRACT

The present application describes an optimized medium for growth of mammalian cells as well as polypeptide production. The cell culture medium is characterized by a Sow ratio of sodium to potassium ions, it further relates to the method of producing polypeptides using such cell culture media. Sn another aspect, the method of polypeptide production can also comprise a temperature shift and/or a pH-shift to further optimize growth and product yield.

27 Claims, 3 Drawing Sheets

(56) References Cited

OTHER PUBLICATIONS

Parker et al, "Identification of the Extracellular Matrix Binding Sites for Insulin-like Growth Factor-binding Protein 5*", The Journal of Biological Chemistry, vol. 271, No. 23, p. 13523-13529 (1996).
Burgener et al, Chapter 3: Medium Development, Cell Culture Technology for Pharmaceutical and Cell-Based Therapies, Eds Ozturk and Hu, Taylor Francis, pp. 41-79 (2006).
Yamane et al, An Autoclavable Powdered Culture Medium for Mammalian Cells, Proceed. of the Soc. for Experim. Biol, and Med., vol. 127, pp. 335-336 (1968).
Alonso, M et al., "Relationship between Membrane Permeability and the Translation Capacity of Human HeLa Cells Studied by Means of the Ionophore Nigericin", European Journal of Biochemistry, vol. 118: 289-294 (1981).
Bavister et al., "Alteration of Extracellular Cation Concentrations and Ratios in Culture Medium does not Affect First Cleavage Division of Hamster Zygotes in vitro nor Overcome the Two-cell Block," Reproduction, Fertility and Development, vol. 1:231-236 (1989).
Borys et al., "Culture pH Affects Expression Rates and Glycosylation of Recombinant Mouse Placental Lactogen Proteins by Chinese Hamster Ovary (CHO) Cells," Nature Biotechnology, vol. 11:720-724 (1993).
Composition of BME without glutamine, 2 pages (2010) URL found online at <https://www.thermofisher.com/us/en/home/technical-resources/media-formulation.4.html>; retrieved on Jun. 3, 2021.
Fukuda et al., "Potassium Ion Enhances Tissue-Type Plasminogen Activator Expression in Cultured HEL Cells," Journal of Fermentation and Bioengineering, vol. 76(2): 111-116 (1993).
Gomez, N. et al., "Effect of Temperature, pH, Dissolved Oxygen, and Hydrolysate on the Formation of Triple Light Chain Antibodies in Cell Culture," Biotechnol. Prog., vol. 26(5):1438-1445 (2010).
Ha, B. et al., "Kainate-induced excitotoxicity is dependent upon extracellular potassium concentrations that regulate the activity of AMPA/KA type glutamate receptors", Journal of Neurochemistry, vol. 83: 934-945 (2002).
Ham, R.G, "Clonal Growth of Mammalian Cells in a Chemically Defined, Synthetic Medium", Proceedings of the National Academy Sciences, vol. 53: 288-293 (1965).
Hossler, P et al., "Optimal and consistent protein glycosylation in mammalian cell culture," Glycobiology, vol. 19(9) 936-949 (2009).
Kagawa et al., "Cytosol type electrolyte medium suitable for long term growth of human cells with very low membrane potential ," Biochemical and Biophysical Research Communications, vol. 169(3):1217-1221 (1990).
Katsuta et al., "Improved Synthetic Media Suitable for Tissue Culture of Various Mammalian Cells", Methods in Cell Biology, Chapter 13, pp. 145-158 (1976).
Kaufman et al., "Depletion of Manganese within the Secretory Pathway Inhibitors O-Linked Glycosylation in Mammalian Cells," American Chemical Society, vol. 33 (33): 1 page (1994).
Kim, S et al., "Differences in Optimal pH and Temperature for Cell Growth and Antibody Production between Two Chinese Hamster Ovary Clones Derived from the Same Parental Clone," Journal of Microbiology and Biotechnology, vol. 17(5): 712-720 (2007).
Oguchi et al., "pH Condition in Temperature Shift Cultivation Enhances Cell Longevity and Specific hMab Productivity in CHO Culture," Cytotechnology, vol. 52:199-207 (2006).
Petronini et al., "Control of Protein Synthesis by Extracellular Na+ in Cultured Fibroblasts", Journal of Cellular Physiology, vol. 140: 202-211 (1989).
Schaarschmidt, G. et al., "A new culturing strategy improves functional neuronal development of human neural progenitor cells", Journal of Neurochemistry, vol. 109:238-247 (2009).
Yoon et al., "Adaptation of Chinese Hamster Ovary Cells to High Potassium Ion-Containing Medium for Enhancement of Follicle-Stimulating Hormone Production," Biotechnology and Bioprocess Engineering, vol. 12:399-403 (2007).
Yoon et al., "Effect of Culture temperature on follicle-stimulating hormone production by Chinese hamster ovary cells in a perfusion bioreactor", Applied Microbiology Biotechnology, vol. 76: 83-89 (2007).
Zhong et al., "High K+ and IGF-1 Protect Cerebellar Granule Neurons Via Distinct Signaling Pathways", Journal of Neuroscience Research, vol. 75:794-806 (2004).
International Search Report and Written Opinion received for PCT Patent Application No. PCT/EP2011/056507, mailed on Jun. 9, 2011, 7 pages.
International Search Report and Written Opinion received for PCT Patent Application No. PCT/EP2011/056508, mailed on Jun. 28, 2011, 7 pages.
International Preliminary Report on Patentability received for PCT Patent Application No. PCT/EP2011/056508, mailedon Nov. 8, 2012, 5 pages.
International Preliminary Report on Patentability received for PCT Patent Application No. PCT/EP2011/056507, mailed on Dec. 27, 2012, 5 pages.
Non-Final Office Action received for U.S. Appl. No. 13/643,996, mailed on Jun. 7, 2013, 15 pages.
Fukuda et al., Journal of Fermentation and Bioengineering, vol. 76, No. 2, 111-116 (1993).
Bavister and Golden~Raprod. Fertil. Dev, 1, 231-236 (1989).
Charity, Waymouth, "The cultivation of cells in chemically defined media and the malignant transformation of cells in vitro" Tissue culture, 1965.
Composition of BME without glutamine: https://www.thermofisher.com/us/en/home/technical-resources/media-formula- tion.4.html, Oct. 21, 2015.
ThermoFisher Scientific, "Neurobasal Medium (1X)", [cited Oct. 13, 2015] Available from: [www.thermofisher.com/de/de/home/technical-resources/media].
Encyclopedia of Industrial Biotechnology Bioprocess, Bioseparation and Cell Technology, "Animal Cell Culture Media by Natarajan Vijayasankaran" North California: John Wiley & Sons Inc., Apr. 15, 2010, 261-27 4.
Exhibit 1, Detailed amino acid composition of medium 'KN!#' as described in Kagawa, Oct. 21, 2015.
Exhibit 2, Recipe of the "1x medium" as described in US-A1 2006/0148074, Oct. 21, 2015.
Exhibit 3, Manganese concentration in "Medium 5" of WO-A2-2006/026408, Oct. 21, 2015.
Exhibit 4, Formulation of "Medium 5" (="12x Medium 4") of WO-A2-2006/026408, Oct. 21, 2015.

* cited by examiner

CELL CULTURE MEDIUM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application is a U.S. National Phase patent application of PCT/EP2011/056508, filed Apr. 25, 2011, which claims priority to U.S. Provisional patent application Ser. No. 61/327,836, filed Apr. 26, 2010, all of which are hereby incorporated by reference in the present disclosure in their entirety.

TECHNICAL FIELD OF THE INVENTION

This invention relates to the general field of biotechnology, particularly the cultivation of cells and their use for the production of polypeptides at industrial scale.

The present invention provides cell culture media which are suitable for the cultivation of cells with high cell viabilities, preferably mammalian cells like CHO cells, and which are characterized by their molar ratio of sodium to potassium ions. The cell culture media according to the present invention allow obtaining high polypeptide productivities when used for the production of a polypeptide, in particular by recombinant expression of polypeptides in mammalian cell culture systems, in particular at industrial scale.

TECHNICAL BACKGROUND OF THE INVENTION

The preparation of polypeptides using recombinant technology has developed into a standard procedure during the last couple of decades. The access to recombinant polypeptides by cloning the genes encoding the respective polypeptide followed by subsequent transformation of suitable expression hosts with the gene to be expressed and final production and purification of the obtained recombinant polypeptide product has provided access to a whole new class of biologically designed and produced therapeutics.

Pharmaceutically active compounds have been prepared in increasing numbers in the pharmaceutical industry using recombinant DNA technology followed by production processes developed in the field of bioengineering.

Such biological products include monoclonal antibodies, which have been developed into important treatment options in various medical fields including autoimmune diseases, inflammatory disorders, immunosuppression oncology or the like.

Development of such therapeutics of biological origin requires production at industrial scale thereby providing access to large amounts of recombinant polypeptide. Preferred expression systems are mammalian cell cultures which are superior to most other eukaryotic systems based on insect cells, yeast or the like, or even traditional prokaryotic expression systems.

However, mammalian cell culture includes tremendous challenges especially at the industrial scale. Production facilities for mammalian cell culture require thorough optimization of many process conditions.

One of the most important process parameters for controlling the overall production process is the medium in which cells are grown and polypeptide production takes place. Suitable cell culture media must provide cell cultures with all necessary nutrient substances, which is especially difficult if no components of animal origin like serum or proteins, e.g. growth factors, are added to the media.

Consequently, a great variety of different cell culture media have been developed. In some cases, the focus has been on the general composition and media with a large variety of different substances have been proposed (U.S. Pat. No. 5,122,469, EP 0 481 791, EP 0 283 942). In other cases, particular ingredients have been suggested to improve cell culture. Major goals have been to improve either growth or survival of the cells, or the quantity and quality of recombinantly expressed polypeptides.

Specific aspects addressed in prior art documents are amongst others the contribution of particular trace ions (e.g. WO 02/066603, EP 0 872 487, EP 1 360 314 A2), vitamins such as ascorbic acid (e.g. U.S. Pat. No. 6,838,284), carbohydrates (EP 1 543 106) or the content of specific amino acids in combination with additional features (e.g. EP 0 501 435, U.S. Pat. No. 5,830,761, U.S. Pt. No. 7,294,484).

The major ions and their concentrations in cell culture media are largely kept constant and remain unconsidered and unchanged. All classical types of media such as e.g. DMEM, DMEM/F12. BME or RPMI 1640 use relatively narrow and fixed ranges for the concentrations of bulk ions in general and the monovalent cations $Na^+$ and $K^+$ in particular. This is in line with the fact that the ionic balance of the bulk ions in general and the monovalent cations $Na^+$ and $K^+$ in particular is a rather universal property of almost all mammalian cells.

In more detail, the transmembrane gradient of sodium and potassium ions is a basic property of mammalian cells with high concentration of potassium ions inside the cell and high concentration of sodium ions outside the cell. The sodium potassium pump is one of the major ion pumps of the cell membrane which is electrogenic and contributes in establishing and maintaining the respective sodium and potassium ionic gradient across the membrane (Kaplan, Membrane cation transport and the control of proliferation of mammalian cells. Annu Rev Physiol.; 40: 19-41 (1978)). The pump uses about 30% of the cells energy and is one of the major energy consuming processes of the cells. Many basic biochemical processes are coupled to the electrochemical gradient of sodium ions, such as e.g. the $Na^+/Ca^+$ exchanger or the amino acid transport into cells. The concentrations of sodium and potassium ions outside a cell are therefore parameters of paramount importance that influence the gradient of these ions across the membrane and the basic status of the cell.

In accordance with the typical concentration of sodium ions inside and outside a generic mammalian cell (Alberts et al., Molecular Biology of the Cell (1994)) mostly sodium concentrations of about 145 mM are chosen together with potassium ion concentrations of around 5 mM. For most media types this results in a ratio between sodium and potassium ions that ranges between about 20-30 (see Table 1 below and e.g. U.S. Pat. No. 5,135,866).

Only few prior art documents describe cell culture media suitable for mammalian cell culture or the production of recombinant proteins mentioning specific ratios of sodium to potassium ions. These documents suggest media compositions with specifically high ratios in the high range of about 30.7 in U.S. Pat. No. 5,232,848, or in a range of between about 25 and 35 thus reaching even higher values (EP 0 283 942, EP 0 389 786). Other media such as HAM's-F12 or defined animal cell culture media as proposed in US 2008/0261259 also specifically suggest higher values (e.g. 27.9 to 57.5 in US 2008/0261259). Only very few documents disclose media having a ratio of sodium to potassium ions below 20, such as 11.5-30 (U.S. Pat. No. 7,294,484) or a ratio of about 15 (U.S. Pat. No. 6,180,401). These documents still use ratios of higher than 10 and also do not assign a particular advantage to changing this parameter to the values as mentioned.

In addition to the effects related to the ionic balance between particular ions, also the contribution of the major ions to the overall osmolality of the medium has to be considered. Most conventional media such as e.g. DMEM, MEM alpha, or Fischer's medium are characterized by a high amount of sodium chloride.

WO 02/101019 addresses the high content of glucose in the medium in combination with usage of a higher osmolality. The high glucose concentration between about 2-40 has been achieved by reducing or even completely eliminating agents such as sodium chloride thereby maintaining osmolality at a given level.

Considering the above challenges and existing disadvantages, there is a continued need in the field of industrial biotechnology for improved cell culture media which allow producing recombinant polypeptides at an industrial scale.

SUMMARY OF THE INVENTION

The present invention provides cell culture media with a reduced $Na^+/K^+$ ratio, i.e. a $Na^+/K^+$ ratio below a value of about 10. This is achieved by means of decreasing the number of total sodium ions and increasing the total potassium ion content. It has been found that such low ratio exerts several beneficial effects, in particular improved viability, growth and productivity of mammalian cells.

Thus, the present invention provides an optimized cell culture medium for the growth of mammalian cells as well as for polypeptide production which is characterized by a ratio of sodium to potassium ions, measured as molar content, of between about 10 to 1 and about 1 to 1, alternatively between about 8 to 1 and about 6 to 1. Implementation of this feature may include concentrations of sodium ions in the range between about 50 and about 90 mM and of potassium ions between about 8 and about 12 mM.

In another aspect, optimization of the cell culture medium includes selecting a total amino acid content of between about 40 mM and about 100 mM, alternatively between about 50 mM and about 100 mM. This feature may be combined with a particular low molar ratio between the total ion and the total amino acid concentration of about 1.9 to about 4.

In a further aspect, the invention provides a process where the cell culture medium according to the invention is used for culturing mammalian cells for the production of a desired recombinant polypeptide. The process involves culturing mammalian cells in a medium according to the invention and expressing the recombinant polypeptide.

Some implementations of the process include culture conditions where the temperature and/or the pH of the medium are shifted at least once during culturing. As a further option feeding is accomplished by a fed batch process.

The desired polypeptide products include glycosylated polypeptides and in particular antibodies and antibody fragments.

The mammalian cells used in the process of the present invention are preferably selected from the group consisting of CHO cells, HEK cells and SP2/0 cells.

In a further aspect, the present invention relates to a process for the production of a cell culture medium according to the invention wherein the different components are admixed with each other. In particular, the concentration of sodium chloride added to the medium composition may be in the range between about 7 and about 15 mM. The concentration of potassium chloride may be added to the medium composition may be in the range between about 8 to about 12 mM.

BRIEF DESCRIPTION OF THE DRAWINGS

The invention will be better understood by reference to the following examples and figures. The examples, however, are not intended to limit the scope of the invention.

DETAILED DESCRIPTION OF THE INVENTION

Figure 1:
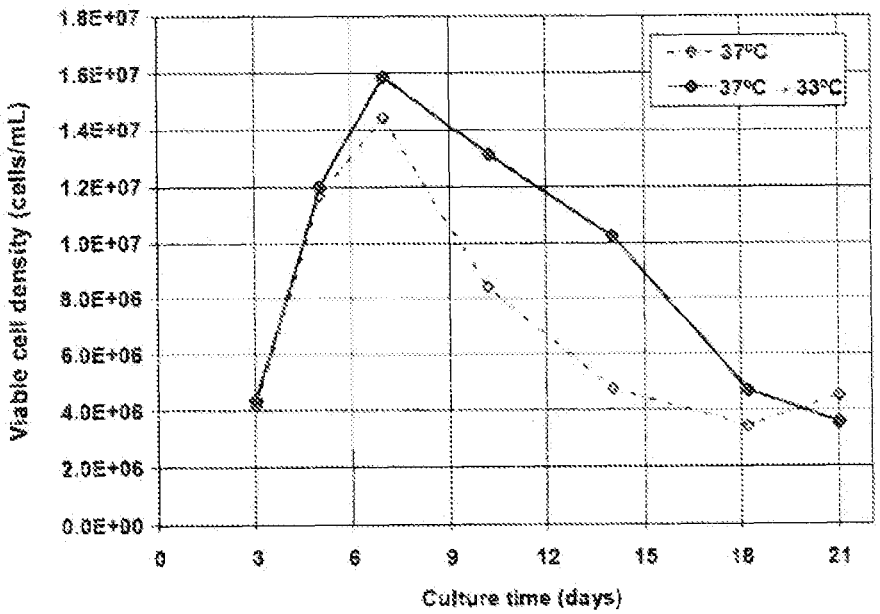
FIG. 1 shows the viable cell density of a mAb1-producing CHO cell clone as function of culture time in shake flask cultures (see Example 1) using a medium with a reduced $Na^+/K^+$ ratio as described by the invention. In addition the effect of a constant temperature versus a temperature shift is depicted.

The cell culture media according to the present invention are used for growing mammalian cells, preferably CHO cells, HEK cells and SP2/0 cells, and for the production of recombinant polypeptides using such cells. CHO cells are especially preferred. The term cell culture medium refers to an aqueous solution of nutrients which can be used for growing cells over a prolonged period of time. Typically, cell culture media include the following components: A source of energy, which will be usually a carbohydrate compound, preferably glucose, amino acids, preferably the basic set of amino acids, including all essential amino acids, vitamins and/or other organic compounds which are required at low concentrations, free fatty acids, and inorganic compounds including trace elements, inorganic salts, buffering compounds and nucleosides and bases.

The cell culture medium according to the present invention can be used in various cell culture processes. Cultivation of cells can be carried out in adherent culture, for instance in monolayer culture or preferably in suspension culture.

The use of cell culture media in the field of pharmaceutical industry, for instance for the production of therapeutically active recombinant polypeptides, does generally not allow the use of any material of biological origin due to safety and contamination issues. Therefore, the cell culture medium according to the present invention is preferably a serum- and/or protein-free medium. The term "serum- and/or protein-free medium" represents a fully chemically defined medium, containing no additives from animal source like tissue hydrolysates, e.g. fetal bovine serum or the like. Further, proteins, especially growth factors like insulin, transferrin or the like are also preferably not added to the cell culture according to the present invention. Preferably, the cell culture medium according to the present invention is also not supplemented with a hydrolysed protein source like soybean, wheat or rice peptone or yeast hydrolysate or the like.

The osmolality and pH of the media are adjusted to values that allow the growth of the cells, e.g. at values between about pH 6.8 and about pH 7.2. The osmolality of the media at the beginning of culturing is typically between about 280 and about 365 mOsm, but may also gradually increase during culturing and the addition of feeding solutions to values of less than or about 600 mOsm/kg. Preferably the media according to the present invention have an initial osmolality of between about 285 and about 365 mOsm/kg.

The temperature of the cell culture is selected in a range where cells are viable and grow. A typical temperature for cell culturing is in the range between about 30° C. and about 38° C. For instance, the cells are initially grown at temperatures of about 36 to about 37° C. which is optimal for CHO cells. However, the exact temperature can be adapted to the needs of the cells and also changed during culturing to allow their optimal viability, growth or production.

The first aspect of the invention is related to the ionic balance between sodium and potassium ions in the cell culture. The present invention describes a molar ratio of sodium to potassium ions which is between about 10 to 1 and about 1 to 1. In further implementations of the invention the ratio is selected between about 9 to 1 and about 5 to 1. Alternatively the ratio is between about 8 to 1 and about 6 to 1.

The concentration of the sodium and potassium ions and the respective ratio is here defined via their molar content. The concentration of sodium and potassium ions is determined by calculating the total number of these ions in the growth medium, after the respective salts have been added and dissolved in the medium solution.

To reach the required sodium concentration usually different salts are added to the medium. Commonly used sodium salts are e.g. NaCl, mono- or dibasic sodium phosphate salts, sodium carbonate, sodium citrate, trace ions such e.g. sodium selenite, but are not limited to these examples. Also the base sodium hydroxide (NaOH) that may be added to the media for pH adjustment contributes to the total content of sodium ions. The term ion in this respect refers to the dissociated state. Calculating the molar content of ions thus means taking into account the valence of the ions. 1 mM sodium chloride (NaCl) added to a medium would therefore contribute 1 mM of sodium ions, while 1 mM dibasic sodium phosphate ($Na_2HPO_4$) would accordingly contribute 2 mM of sodium ions. According to the invention the sodium concentration used in the media is between about 50 and 90 mM. Alternatively the sodium ion concentration is selected to be about 65 to about 85 mM.

The potassium salt that is used for media typically is KCl but also includes e.g. $K_2SO_4$ or potassium dihydyrogen phosphate ($KH_2PO_4$). The potassium salt is not limited to these particular examples. Alternatively, the potassium concentration used in the media is between about 8 and about 12 mM, or about 10.7 mM.

Table 1 shows examples for media that are traditionally used for the growth of mammalian cells. These classic media such as DMEM, DMEM/F12, BGJ and others have a particularly high ratio of Na/K ions. The media according to the present invention are characterized by a particularly low Na/K ratio of less than about 10 to 1 (see Table 2). The media according to the present invention are suitable for culturing CHO and other mammalian cells and show an improved growth of the cells and/or allow for an improved production of polypeptides. Two examples for such media are shown in Table 3, which depicts the composition of two media examples and how a low Na/K ratio can be achieved. Synergistic effects between the low ratio of sodium to potassium ions and the other media features have even an additional advantageous effect on growth of cells and production of recombinant proteins.

In addition to the particular concentration of sodium and potassium ions and their specific ratio, the present media are also characterized by a particularly low concentration of sodium chloride (NaCl) that is added to the mixture of media components. Preferably concentrations of about 7 to about 15 mM are used. This low amount of sodium chloride is unusual. In some implementations of the present invention, the sodium chloride concentration (in mM) is even lower than the concentration (in mM) of the respective potassium salt that is added. Furthermore, media according to the present invention often show a low total content of chloride ion. As shown by the examples of Table 2, this results in initial chloride concentrations of between about 36 and 46 mM. Mostly inorganic salts such as NaCl or $CaCl_2$ contribute to this value, but also media components such as choline chloride, or amino acids such as for example L-histidine hydrochloride or L-lysine hydrochloride may add on to the total concentration.

A further advantage of the media compositions according to the present invention is the combination of a low molar Na/K ratio together with a starting concentration of amino acids that ranges between about 40 mM, alternatively about 50 mM and about 100 mM. Classical media use comparatively low concentrations of amino acids and/or high Na/K ratios. The combination of both features may provide additional effects that are advantageous for the growth of the cells and the production of polypeptides.

Table 2 shows different implementations of these parameters according to the invention. In addition to their total amino acid content suitable media according to the present invention optimized for cell growth preferably contain initial amino acid concentrations according to the following ranges.

| Amino acids | Conc. (mmol/L) |
|---|---|
| Arginine, free base | 4.0-6.0, preferably 4.5-5.5 |
| Asparagine monohydrate | 3.0-6.0, preferably 4.0-5.5 |
| Aspartic acid | 2.5-4.0, preferably 3.0-3.6 |

-continued

| Amino acids | Conc. (mmol/L) |
|---|---|
| Glycine | 0.3-0.8, preferably 0.5-0.7 |
| Histidine, HCl $H_2O$ | 0.6-1.0, preferably 0.7-0.9 |
| Isoleucine | 2.0-5.0, preferably 2.9-4.0 |
| Leucine | 3.0-7.0, preferably 3.5-6.0 |
| Lysine HCl | 2.0-4.0, preferably 2.5-3.5 |
| Methionine | 1.0-1.5, preferably 1.2-1.4 |
| Phenylalanine | 1.0-2.0, preferably 1.3-1.8 |
| Proline | 2.5-6.0, preferably 3.0-5.5 |
| Serine | 3.0-8.0, preferably 4.0-7.0 |
| Threonine | 2.0-3.5, preferably 2.5-3.1 |
| Tryptophane | 0.4-1.0, preferably 0.5-0.8 |
| Valine | 2.5-5.0, preferably 3.0-4.5 |
| Tyrosine | 1.0-2.0, preferably 1.2-1.8 |
| Cystine | 0.5-1.0, preferably 0.6-0.9 |
| Glutamine | 5.5-9.5, preferably 6.2-8.2 |

The media of the present invention further specified by amino acids as defined in the above table can be favourably used in the improved cell culture processes according to the present invention.

In a particularly preferred embodiment media according to the present invention are optimized for production and preferably contain initial amino acid concentrations according to the following ranges.

| Amino acids | Conc. (mmol/L) |
|---|---|
| Arginine, free base | 4.0-6.0, preferably 4.5-5.5 |
| Asparagine monohydrate | 9.0-11.0, preferably 9.5-10.5 |
| Aspartic acid | 2.5-4.0, preferably 3.0-3.6 |
| Glycine | 0.3-0.8, preferably 0.5-0.7 |
| Histidine, HCl $H_2O$ | 1.0-1.5, preferably 1.1-1.3 |
| Isoleucine | 5.5-7.0, preferably 6.0-6.9 |
| Leucine | 8.0-10.0, preferably 9-9.2 |
| Lysine HCl | 3.0-6.0, preferably 4.0-5.0 |
| Methionine | 1.5-2.5, preferably 1.5-2.0 |
| Phenylalanine | 2.0-3.5, preferably 2.5-3.0 |
| Proline | 7.5-9.0, preferably 8.0-8.5 |
| Serine | 10.5-13.0, preferably 11.0-11.9 |
| Threonine | 3.5-5.5, preferably 4.0-5.0 |
| Tryptophane | 0.9-2.0 preferably 1.0-1.4 |
| Valine | 5.5-7.5, preferably 6.0-6.8 |
| Tyrosine | 1.0-3.0, preferably 2.0-2.5 |
| Cystine | 0.5-2.0, preferably 1.0-1.3 |
| Glutamine | 5.5-9.5, preferably 6.2-8.2 |
| Glutamic acid | 0.5-2.5, preferably 1.0-1.2 |

Production media containing amino acids as defined in the above table can be favourably used in the improved cell culture processes according to the present invention.

In a further aspect of the invention, in addition to the specific ratio between sodium and potassium ions, also the overall balance between total ion concentrations (contributing to the overall ionic strength of the medium), and the amino acids in the medium is important. The ratio between the total ion concentration and the amino acids in the nutrient growth medium is mostly dominated by bulk inorganic salts such as e.g. sodium chloride, potassium chloride, sodium hydrogen carbonate and others, that are major ingredients of most types of cell culture media for animal cells. Also salts of trace ions, amino acids or vitamins contribute to this value (e.g. cupric sulphate, L-arginine hydrochloride, L-histidine hydrochloride, choline chloride, 0-calcium pantothenate and others). It may be advantageous for the cells to also adjust the concentrations of these ions. We therefore define the total concentration of ions here as the sum of all major organic and inorganic salts added to the medium which are ionizable in an aqueous medium solution plus the base NaOH and acid HCl. Trace elements are not included. Thus, 1 mM of NaCl, NaOH or the organic salts such as Lysine-HCl or choline chloride would contribute each 2 mM of ions. 1 mM of $MgCl_2$ would accordingly add 3 mM of ions while 1 mM of the organic salt trisodium citrate contributes with 4 mM.

According to the present invention the molar ratio between ions and amino acids is thus selected to be between about 1.9 and 4. In some implementation the ratio is selected to range between about 2.0 and 3.9. These particular low ratios are not only reached by a relatively high content of amino acids but also by a relatively low molar content of ions in the medium. The content of ions in the medium generally is less than 250 mM. For instance, the values are selected to be between about 150 and 220 mM, or alternatively between about 170 and 200 mM.

In summary, the described particular media features have important effects on cellular metabolism and physiology while at the same time also affecting general parameters such as osmolality or e.g. availability of nutritional components. The balance of the different media features thus lead to unique properties that lead to unexpected synergistic effects for the cells.

The media with a low Na/K ratio are generally suitable for growth of different mammalian cells and the manufacturing of recombinant polypeptides/proteins in large scale production. The polypeptides and proteins as used herein refer to recombinant polypeptides that are expressed by the respective mammalian cell after transfection of the cells with the DNA construct or constructs coding for the product of interest. Any polypeptide that can be expressed in a host cell may be produced according with the present invention. After the polypeptide(s) has/have been produced by the process of the present invention it is either extracellularly secreted, bound to the cells or remains in the cells, depending on the specific product and cell line used. The polypeptide product can be recovered from culture supernatant directly or after lysis of the cells by standard procedures. Also further isolation and purification is done by the standard techniques known to the skilled person. The polypeptide of the invention can also be included in a pharmaceutical composition.

Another aspect of the invention relates to a process for the production of a recombinant polypeptide comprising culturing mammalian cells in a medium according to the present invention wherein the culturing conditions comprise at least one temperature shift and/or at least one pH shift.

Accordingly, in another aspect of the invention it may be advantageous to change the temperature during the course of culturing and include one or more temperature shifts that are initiated at certain time points. A change/shift in the temperature does not refer to spontaneous fluctuations in the temperature, but to changes in temperature of at least 1° C. or alternatively at least 2° C. that are intended, and where the second temperature is being maintained for at least one day. A change/shift can be implemented by altering the temperature setpoint of the culture. The timing is dependent on either the growth state of the culture, a predetermined number of days after the start of the culture or the metabolic needs of the cells. Thus, the temperature may be shifted in a period of about 1 to 10 days after starting the culture. Preferably a temperature shift is done during the growth phase of the cells or towards the end of this phase. Depending on the culture vessel volume, the change may occur rapidly or more slowly and lasts several hours. In one example such a shift in temperature is implemented during the growth phase of the culture when the density is between about 40 and about 90% of the maximal density. In one example the first temperature is between about 33 and about 38° C. while in other examples the first temperature is between about 36 and about 38° C. The second temperature is between about 30 and about 37° C., or alternatively between about 32 and about 34° C.

In another aspect of the present invention it may be advantageous to change the pH during the course of the culturing by including one or more pH shifts. In further aspects of the invention shifts in temperature may also be combined with one or more shifts in the pH. While the first pH (e.g. pH of 7.0) is chosen to be favourable for rapid expansion of the cells it is advantageous to modify the pH of the culture, once a certain cell density is reached. This change or shift in pH is accomplished by changing the pH setpoint of the bioreactor/culture vessel or by defining a pH setpoint in combination with a deadband. A pH change does not refer to small fluctuations in the pH, it rather refers to an intended change. The second pH value (e.g. 6.8) is selected to reduce cell death and to allow high cell-specific production rates of polypeptides of adequate quality. The second pH can be maintained until the end of culturing or additional pH shifts may be introduced. In one implementation it may be useful to change the pH by at least 0.2 in one embodiment the first pH is selected to be in the range between pH 6.8 and 7.5. In another embodiment the first pH is selected to be in the range between pH 6.8 and 7.2. The second pH value that is reached after the shift in pH may be in the range between pH 6.0 and pH 7.5, or alternatively between 6.5 and 6.8.

The cell culture medium according to the present invention can be used in various cell culture processes. Cultivation of cells can be carried out in adherent culture, for instance in monolayer culture or preferably in suspension culture.

Large scale cultivation of cells can be used for instance by the various fermentation processes established in industrial biotechnology. Continuous and discontinuous cell culture processes can be utilized using the cell culture media according to the present invention. Other known reactor technologies, e.g. perfusion technologies or the like can be also utilized. Batch processes are one preferred embodiment.

The batch cell culture includes fed-batch culture or simple batch culture. The term "fed batch cell culture" refers to cell culture wherein mammalian cells and cell culture medium are supplied to the culturing vessel initially and additional culture nutrients are fed continuously or in discrete increments to the culture during the culturing process with or without periodic cell and/or product harvest before termination of the culture. The term "simple batch culture" relates to a procedure in which all components for cell culturing including the mammalian cells and the cell culture medium are supplied to the culturing vessel at the start of the culturing process.

According to one preferred embodiment of the present invention feeding of the cultures is done in a fed batch process. Such feeding is beneficial for the cells to replace media components and nutrients that are depleted in the media during the culture process. Typically feed solutions comprise amino acids, at least one carbohydrate as an energy source, trace elements, vitamins or specific ions. The feed solutions are added depending on the needs of the cells, which are either based on a predetermined schedule that has been determined for the particular cell line or cell clone and product or measured during the culture process. It is particularly advantageous to use concentrated feed solutions in order to avoid large volume increase and dilution of the media. In some embodiments it may also be useful to have at least two different feed solutions. This allows independent dosing of two or more different groups of nutrients and components to the cells and thus a better adjustment of the feeding conditions concerning optimal supply of certain nutrients.

In a further embodiment of the invention, one of the two feed solutions added to the cell culture medium is a feed comprising the dipeptide cystine and the amino acid tyrosine. Preferably, the feed contains the dipeptide cystine and the amino acid tyrosine at respective concentrations in the range of about 6.5 V and about 8.0 g/l and in the range of about 9 g/l and about 11 g/l in an aqueous solution at a basic pH of above 10. In a particular embodiment, the concentrated feed comprises the dipeptide cystine and the amino acid tyrosine at respective concentrations of 10.06 g/l L-tyrosine and 7.25 cystine at a pH of above 10.

The feed medium comprising cystine and tyrosine as described above can be added either based on the measured consumption of the respective amino acids or according to a fixed schedule at e.g. about 0.2 to about 0.8 wt % of the initial cell culture medium weight per day, preferably at about 0.4 wt % of the initial cell culture medium weight per day.

In some examples the other feed solution contains all other amino acids that are also present in the basic medium except tyrosine and cystine. In some examples this additional feed solution may consist of particular selected components such as e.g. amino acids or carbohydrates. In a further preferred embodiment of the invention this concentrated feed medium preferably contains selected amino acids according to the following concentration ranges.

| Amino acids | Feed Medium Conc. (mmol/L) |
|---|---|
| Arginine, free base | 12.0-17, preferably 13.5-16.0 |
| Histidinie, HCl $H_2O$ | 5.5-7.5, preferably 5.9-7.0 |
| Isoleucine | 21-28.0, preferably 22.0-27 |
| Leucine | 32-42, preferably 34.5-40.0 |
| Lysine HCl | 17.0-22.0, preferably 17.5-21.5 |
| Methionine | 5.5-8.0, preferably 6.0-7.5 |
| Phenylalanine | 8.5-12.0, preferably 9.0-10.5 |
| Proline | 18.0-24, preferably 18.5-22.0 |
| Serine | 39.0-49.0, preferably 39.5-46.5 |
| Threonine | 14.5-19.0, preferably 15.0-18.5 |
| Tryptophane | 3.0-5.0, preferably 3.5-4.9 |
| Valine | 23.0-29.0, preferably 23.8-27.5 |
| Glutamine | 175.0-220.0, preferably 176.0-201 |

Preferably also carbohydrates such as glucose are added to this concentrated feed medium, preferred concentrations being between about 1200 and about 1400 mmol/l, or alternatively between about 1300 and about 1395 mmol/l.

The feed medium as lust described, preferably including a carbohydrate, such as glucose, can be added either based on the measured consumption of the respective amino acids or according to a fixed schedule at e.g. about 1 to about 4 wt % of the initial cell culture medium weight per day, preferably at about 2 wt % of the initial cell culture medium weight per day.

The cells cultivated in the cell culture medium according to the present invention include mammalian and non-mammalian cells. Non-mammalian cells include insect cells or the like. However, mammalian cells are preferred. The terms cell, cell line and cell culture may be interchangeably used herein.

Examples of mammalian cells include human retinoblasts; human cervical carcinoma cells, human embryonic kidney line, human lung cells, human liver cells, PER.C6 cells (a human retinoblast-derived cell line), human hepatoma line and human cell lines such as AGE1.HN; monkey kidney CV1 line transformed by SV40; monkey kidney cells, African green monkey kidney cells, Chinese hamster ovary cells/-DHFR, baby hamster kidney cells; mouse sertoli cells; mouse mammary tumor, canine kidney cells; buffalo rat liver cells; TRI cells; MRC 5 cells; FS4 cells; CHO cells are a preferred cell line for practicing the invention.

In one preferred embodiment of the invention these cells can be different strains of CHO cells, such as wild type CHO K1, CHO dhfr− (Dux1) or CHO dhfr− (DG44), but also HEK cells, Sp2/0 cells. These cells are typically transfected with one or more DNA constructs that encode the polypeptide(s) of interests. Any polypeptide that can be expressed in these host cells may be produced according with the present invention.

Another class of cells that can be used with the cell culture media according to the present invention include hybridoma cells which are commonly used for the production of monoclonal or polyclonal antibodies.

The polypeptides that can be produced from the cell cultures and the cell culture media according to the present invention are not limited. The polypeptides can be recombinant or not recombinant. The term "polypeptide" as used herein encompasses molecules composed of a chain of more than two amino acids joined by peptide bonds; molecules containing two or more such chains; molecules comprising one or more such chains being additionally modified, e.g. by glycosylation. The term polypeptide is intended to encompass proteins.

The preferred class of polypeptides produced by cell cultures and the cell culture media according to the present invention are recombinant antibodies.

The term "antibody" is used in the broadest sense and specifically covers monoclonal antibodies (including full length monoclonal antibodies), polyclonal antibodies, multispecific antibodies (e.g., bispecific antibodies), nanobodies modified antibodies, subunits of antibodies, antibody derivatives, artificial antibodies, combinations of antibodies with proteins and antibody fragments sufficiently long to display the desired biological activity. The monoclonal antibodies as used herein may be human antibodies.

However, polypeptides other than antibodies can also be produced using cell cultures and the cell culture media according to the present invention, e.g. polypeptides like transmembrane proteins, receptors, hormones, growth factors, proteases, clotting and anti-clotting proteins, inhibitor proteins, interleukins, transport factors, fusion proteins and the like.

The products obtained from such cell culture processes can be used for the preparation of pharmaceutical preparations. The term "pharmaceutical preparation" indicates a composition suitable or adapted to for administration to a mammal, especially a human. In addition, the protein(s) according to the invention can be administered together with other components of biologically active agents such as pharmaceutically acceptable surfactants, recipients, carriers, diluents and vehicles.

Table 1 summarizes compositions of commercially available media and additional cell culture media from the prior art values are based on published values; additions such as NaOH are thus not included in the values. Sodium concentration or the sodium to potassium ratio is thus rather underestimated and even further apart from the values of the present invention.

TABLE 1

| Media | Na+ (mM) | NaCl (mM) | K+ (mM) | Ratio Na/K | Cl− (mM) | Total Ions (mM) | Total AA (mM) | Ratio Ions/AA |
|---|---|---|---|---|---|---|---|---|
| Commercial media | | | | | | | | |
| DMEM/F12 | 123 | 120.6 | 4.2 | 29 | 129.1 | 290 | 7.0 | 41.4 |
| Ham's F12 | 147.0 | 130.1 | 3.0 | 49 | 135.0 | 305 | 4.0 | 76.2 |
| MEM alpha | 145.4 | 117.2 | 5.3 | 27 | 127.0 | 310.2 | 9.0 | 34.5 |
| RPMI 1640 | 138.7 | 103.4 | 5.3 | 26 | 109.0 | 283.6 | 6.6 | 42.9 |
| BME | 144.4 | 117.2 | 5.3 | 27 | 126.4 | 307.1 | 1.4 | 219 |
| Fischer's | 152.3 | 136.8 | 5.3 | 28 | 144.9 | 317 | 5.6 | 56.6 |
| Other media | | | | | | | | |
| U.S. Pat. No. 7,294,484 | 48/125/86 | 19/95/64 | 4.2 | 12/30/21 | not determined | ND | >70 | ND |
| WO 02/101019 Media A/B | 10.9/8.1 | 0/0 | 20.2/19.9 | 0.5/0.4 | 48/31 | 122.8/78.9 | 78.1/59.5 | 1.6/1.3 |

Table 2 discloses cell culture media formulations according to the present invention characterized by their particular low ratio of sodium to potassium ions.

TABLE 2

| Media | Na+ (mM) | NaCl (mM) | K+ (mM) | Ratio Na/K | Cl− (mM) | Total Ions (mM) | Total AA (mM) | Ratio Ions/AA |
|---|---|---|---|---|---|---|---|---|
| Medium 1 | 83.6 | 14.6 | 10.7 | 7.8 | 36.2 | 195.7 | 51.1 | 3.8 |
| Medium 2 | 69.5 | 8.6 | 10.7 | 6.5 | 45.5 | 191.2 | 90.5 | 2.1 |
| Medium 3 | 79.7 | 8.6 | 10.7 | 7.4 | 41.4 | 190.6 | 90.7 | 2.1 |
| Medium 4 | 73.4 | 8.6 | 10.7 | 6.9 | 39.9 | 177.5 | 80.2 | 2.2 |
| Medium 5 | 67.2 | 8.6 | 10.7 | 6.3 | 38.3 | 164.3 | 69.7 | 2.4 |
| Medium 6 | 60.9 | 8.6 | 10.7 | 5.7 | 36.8 | 151.1 | 59.2 | 2.6 |

Table 3 discloses the compositions of examples for chemically defined cell culture media according to the present invention. The individual components of these cell culture media are available from standard commercial sources.

TABLE 3

| Components | Medium 1 Final conc. (mg/l) | Medium 2 Final conc. (mg/l) | Medium 3 Final conc. (mg/l) | Medium 4 Final conc. (mg/l) | Medium 5 Final conc. (mg/l) | Medium 6 Final conc. (mg/l) |
|---|---|---|---|---|---|---|
| $CaCl_2$, anhydr. | 131 | 133.2 | 130.6 | 130.6 | 130.6 | 130.6 |
| KCl, anhydr. | 800 | 800 | 800 | 800 | 800 | 800 |
| $MgCl_2$, anhydr. | 155 | 250.4 | 250.2 | 226.4 | 202.6 | 178.9 |
| NaCl | 850.6 | 500 | 500 | 500 | 500 | 500 |
| Di-Sodium hydrogenphosphate, anhydr. | 710 | 1065 | 1775 | 1508.8 | 1242.5 | 976.3 |
| Sodium hydrogen carbonate, anhydr. | 2500 | 2000 | 2000 | 2000 | 2000 | 2000 |
| L-Arginine, free base | 871 | 871 | — | — | — | — |
| L-Arginin × HCl | — | — | 1053 | 1053 | 1053 | 1053 |
| L-Asparagine, $H_2O$ | 616 | 1501 | 1501 | 1279.8 | 1058.5 | 837.3 |
| L-Aspartic acid | 461 | 461 | 461 | 461 | 461 | 461 |
| L-Cystine | 200.1 | 304.5 | 304.5 | 228.4 | 152.3 | 76.1 |
| L-Glutamic acid Na salt Hydrate | — | 182 | — | — | — | — |
| L-Glutamic acid | — | — | 182 | 136.5 | 91 | 45.5 |
| L-Histidine, HCl—$H_2O$ | 168 | 268 | 268 | 243 | 218 | 193 |
| L-Isoleucsne | 394 | 894 | 894 | 769 | 644 | 519 |
| L-Leucine | 499 | 1199 | 1199 | 1025 | 850 | 675 |
| L-Lysine, HCl | 621 | 821 | 821 | 772 | 722 | 672 |
| L-Methionine | 179 | 279 | 279 | 255 | 230 | 205 |
| L-Phenylalanine | 264 | 464 | 464 | 414 | 364 | 314 |
| L-Proline | 368 | 968 | 968 | 818 | 668 | 518 |
| L-Serine | 432 | 1232 | 1232 | 1032 | 832 | 632 |
| L-Threonin | 333 | 533 | 533 | 484 | 434 | 384 |
| L-Tryptophan | 102 | 252 | 252 | 214.5 | 177 | 139.5 |
| L-Valine | 375 | 775 | 775 | 676 | 576 | 476 |
| L-Tyrosine | 277.7 | 422.5 | 422.5 | 316.9 | 211.3 | 105.6 |
| Glycine | 38 | 38 | 38 | 38 | 38 | 38 |
| L-Glutamine | 1169.2 | 1169.2 | 1169.2 | 1169.2 | 1169.2 | 1169.2 |
| Biotin | 0.4 | 0.4 | 0.4 | 0.4 | 0.4 | 0.4 |
| D-Ca-Pantothenate | 4 | 4 | 4 | 4 | 4 | 4 |
| Folic acid | 5 | 5 | 5 | 5 | 5 | 5 |
| myo-Inositol | 40 | 140 | 140 | 115 | 90 | 65 |
| Nicotinamide | 4 | 4 | 4 | 4 | 4 | 4 |
| Pyridoxine, HCl | 2 | 2 | 2 | 2 | 2 | 2 |
| Riboflavin | 0.4 | 0.4 | 0.4 | 0.4 | 0.4 | 0.4 |
| Vitamins B12 | 2 | 2 | 2 | 2 | 2 | 2 |
| Thiamine, HCl | 4 | 4 | 4 | 4 | 4 | 4 |
| Putrescine, 2HCl | 10 | 110 | 110 | 85 | 60 | 35 |
| Cholin chloride | 40 | 240 | 240 | 190 | 140 | 90 |
| Sodium selenit ($Na_2SeO_3$) | 0.03 | 0.03 | — | — | — | — |
| Sodium selenit Heptahydr. ($Na_2SeO_3 \times 5H_2O$) | — | — | 0.02 | 0.02 | 0.02 | 0.02 |
| Manganese chloride tetrahydrate | 0.3 | 0.3 | 0.3 | 0.3 | 0.3 | 0.3 |
| Ammonium molybdate tetrahydrate | 0.3 | 0.3 | 0.3 | 0.3 | 0.3 | 0.3 |
| Zinc chlorid, anhydr. | 3 | 3 | 3 | 3 | 3 | 3 |
| Cupric chloride dihydrate | 0.3 | 0.3 | 0.3 | 0.3 | 0.3 | 0.3 |
| Cobalt chloride hexahydrate | 0.3 | 0.3 | 0.3 | 0.3 | 0.3 | 0.3 |
| Ethanolamine | 10 | 100 | 100 | 77.5 | 55 | 32.5 |
| Monothioglycerol | 2 | — | — | — | — | — |
| HEPES, acid form | 17870 | 4766 | 4766 | 3574.5 | 2383 | 1191.5 |
| Tri-Sodiumcitrate dihydrate | 911.7 | 1235.2 | 911.2 | 911.2 | 911.2 | 911.2 |
| $FeCl_3 \times 6H_2O$ | 54.1 | 54.1 | 54.1 | 54.1 | 54.1 | 54.1 |
| Pluronic F68 | 1000 | 1000 | 1000 | 1000 | 1000 | 1000 |
| D-Glucose, anhydr. | 10000 | 10000 | 10000 | 10000 | 10000 | 10000 |
| HCl | — | 327.6 | — | — | — | — |
| NaOH | 799.2 | 339.9 | 519.9 | 419.9 | 319.9 | 220 |

EXAMPLES

In the examples described below, chemically defined cell culture media 1 and 2 having the composition as detailed in Table 3 above are used. The individual components of these cell culture media are available from standard commercial sources.

Table 4 below shows the composition of a concentrated feed medium containing L-tyrosine and cystine. The feed medium can be added either based on the measured consumption of the respective amino acids or according to a fixed schedule at e.g. 0.4% wt per day.

TABLE 4

| Components | Feed Medium (g/l) |
|---|---|
| NaOH 32% | 18.7 mL |
| L-Tyrosine | 10.06 |
| Cystine | 7.25 |

Table 5 below shows the composition of an exemplary concentrated feed medium. The feed medium can be added either based on the measured consumption of amino acids or according to a fixed schedule at e.g. 2% wt per day.

TABLE 5

| Components | Feed Medium (g/l) |
|---|---|
| L-Arginine, free base | 2.72 |
| L-Histidinie, HCl—$H_2O$ | 1.44 |
| L-Isoleucine | 3.44 |
| L-Leucine | 5.20 |
| L-Lysine, HCl | 3.72 |
| L-Methionine | 1.08 |
| L-Phenylalanine | 1.72 |
| L-Proline | 2.44 |
| L-Serine | 4.76 |
| L-Threonin | 2.08 |
| L-Tryptophan | 0.88 |
| L-Valine | 3.16 |
| L-Glutamine | 29.23 |
| D-Glucose-monohydrate | 275.00 |
| 25% HCl | 8.25 ml |
| 32% NaOH | 5.6 ml |

For the experiments of the examples a parental CHO cell line is used which is derived from the dhfr (+) CHO-K1 cell line ATCC CCL-61 (Kao et. al., Genetics, 1967, 55, 513-524; Kao et. al., PNAS, 1968, 60, 1275-1281; Puck et. al., J. Exp. Med., 1958, 108, 945-959) by adaptation to serum-free, protein-free media conditions. Two aliquots of this parental cell line are transfected to express two different monoclonal antibodies mAB1 and mAB2, respectively.

Example 1

In Example 1, two shake flask cultures containing medium 1 are inoculated in parallel with a mAb1-producing CHO clone. The shake flask cultures are incubated in a carbon dioxide incubator at 37° C. On day 3, one shake flask is transferred to a carbon dioxide incubator set at 33° C. Both shake flasks are similarly fed with two feed solutions. Feed was supplemented according to a fixed schedule, with addition of 0.4% of the first feed solution (Table 2) and 2% of the second feed (Table 3) per day starting on day 5 and lasting until the end of the culture.

Figure 2:
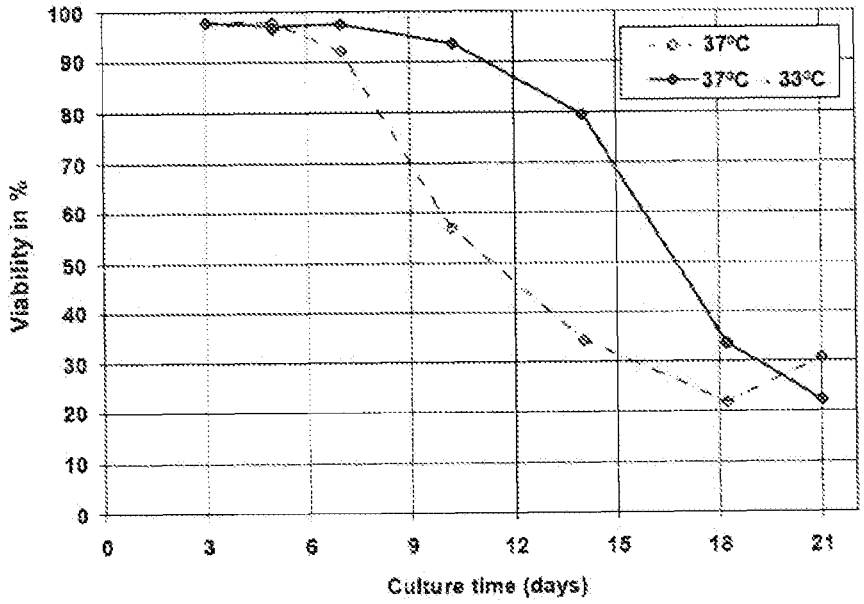
FIG. 2 shows the viability of a mAb1-producing CHO cell clone (see Example 1) using a medium with a reduced $Na^+/K^+$ ratio and the effect of a constant temperature versus a temperature shift on day 3.
Figure 3:
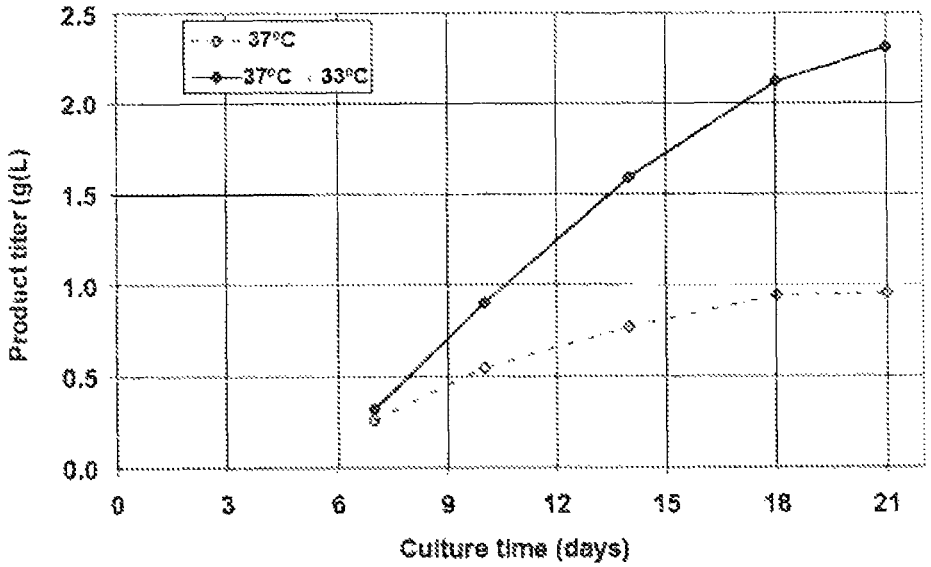
FIG. 3 shows the product titer as function of cultivation time for shake flask cultures of a mAbl-producing the CHO cell done with and without a temperature shift (see Example 1). Cells were cultivated in a medium with a reduced $Na^+/K^+$ ratio according to the invention.

The temperature shift to 33° C. enables longer maintenance of the viable cell density and viability of the culture with time (FIGS. 1 and 2) and the achievement of a higher product titer (FIG. 3), compared to the culture that is maintained at 3° C. for the whole duration of the experiment. This example illustrates the benefit of implementing a temperature shift to 33° C. during a cell culture production process based on a CHO cell line.

Example 2

Figure 4:
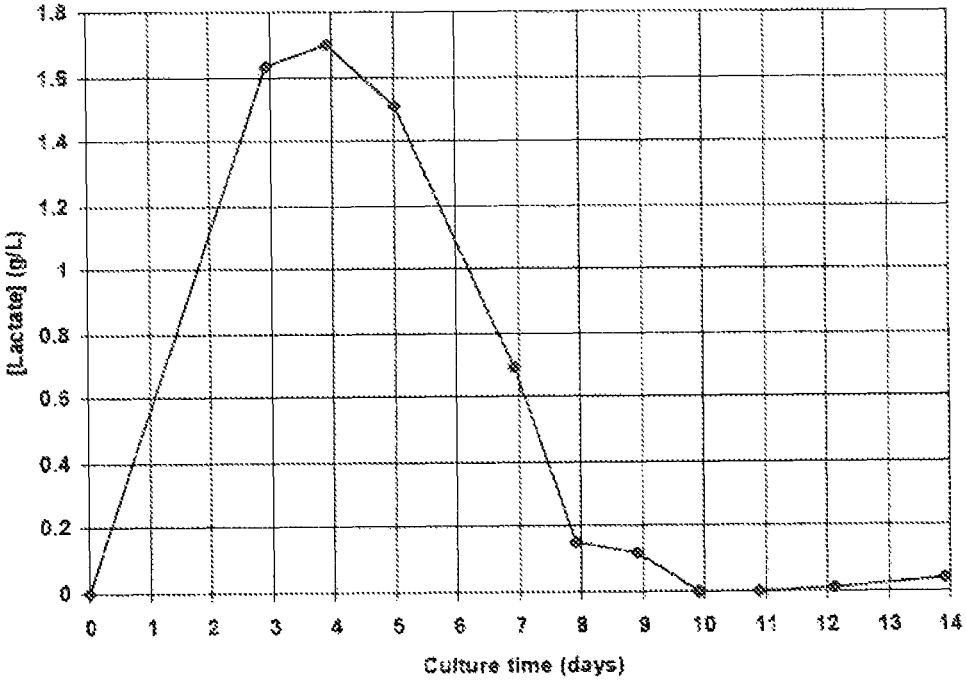
FIG. 4 shows the lactate concentration over cultivation time in a mAb2-producing clone (see Example 2). Cells were cultivated in a medium with a reduced $Na^+/K^+$ ratio according to the invention.
Figure 5:
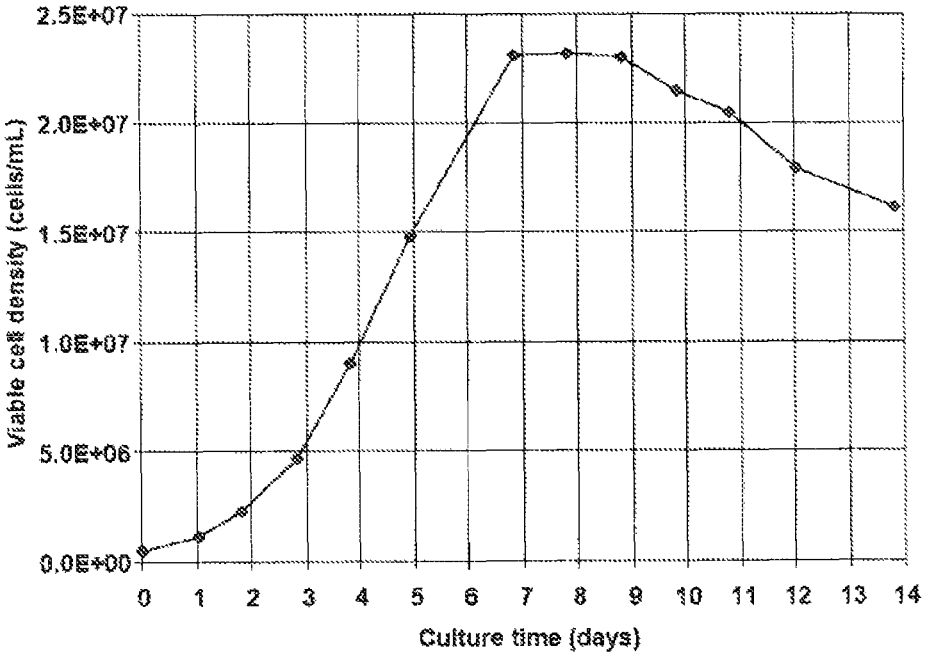
FIG. 5 shows the viable cell density as a function of cultivation time in a 300-L, bioreactor with a CHO cell clone. Culture conditions included a temperature step (day 5) and two pH shifts due to pH regulation with a setpoint and a deadband (also see Example 2). Cells were cultivated in a medium with a reduced $Na^+/K^+$ ratio according to the invention.
Figure 6:
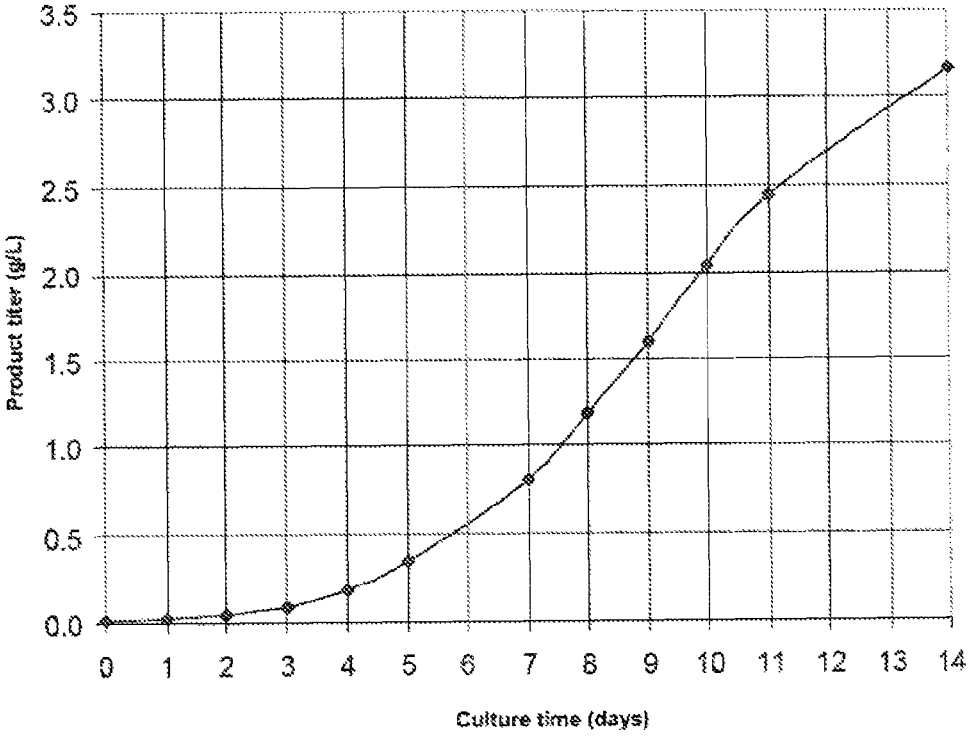
FIG. 6 shows the product titer as function of cultivation time in a 300-L bioreactor with a CHO cell clone. The process combined a temperature with two pH shifts (see also FIG. 5 and Example 2). Cells were cultivated in a medium with a reduced $Na^+/K^+$ ratio according to the invention.

In this example, a 300-1 bioreactor containing medium 2 is inoculated with a mAb2-producing CHO clone. On day 5, the temperature of the bioreactor is shifted from 36.5° C. to 33° C. The pH setpoint is 6.90 and the deadband is 0.10. As a result, the culture starts at pH 7.00, the pH drifts down to 6.80 between day 2 and day 4, and then progressively returns to 7.00 due to lactic acid consumption by the cells (FIG. 4). The shift to pH 6.80 enables to reduce the addition of base compared to a scenario with a constant pH 7.00, The return to pH 7.00 enables to reduce the concentration of $CO_2$ in the medium compared to a scenario where the pH is left at 6.80 after the first shift. In this process that combines temperature and pH shifts, a high viable cell density is reached and the decrease in viable cell density over time is minimized (FIG. 5), allowing to reach on day 14 a high titer (FIG. 6) of product of adequate quality. Feeding is applied similarly as in Example 1.

The invention claimed is:

[1. A serum-free and protein-free cell culture medium for expressing recombinant polypeptides from Chinese Hamster Ovary, Human Embryonic Kidney or SP2/0 myeloma cells having a molar ratio of sodium to potassium ions of between 8 to 1 and 6 to 1, and wherein the sodium ions have a concentration of between 50 and 90 mM.]

[2. The cell culture medium of claim 1 wherein the potassium ions have a concentration of between 8 and 12 mM.]

[3. The cell culture medium of claim 1 comprising a total amino acid concentration between 40 and 100 mM.]

[4. The cell culture medium of claim 3 wherein the molar ratio between the total ion concentration to the total amino acid concentration is between 1.9 and 4.]

[5. A process for the production of a recombinant polypeptide comprising culturing mammalian cells comprising a recombinant nucleic acid encoding the recombinant polypeptide in the medium of claim 1 and expressing the recombinant polypeptide, wherein the mammalian cells are selected from the group consisting of Chinese Hamster Ovary (CHO) cells, Human Embryonic Kidney (HEK) cells, and SP2/0 cells.]

[6. The process according to claim 5 wherein culturing conditions comprise at least one temperature shift and/or at least one pH shift.]

[7. The process according to claim 5, wherein culturing is done by a fed batch process.]

[8. The process according to claim 5 wherein the expressed recombinant polypeptide is glycosylated.]

[9. The process according to claim 5, wherein the expressed polypeptide is an antibody or antibody fragment.]

[10. A process for the production of a cell culture medium according to claim 1 wherein the medium's components are admixed with each other.]

[11. The process according to claim 10 wherein sodium chloride is added at a concentration between 7 and 15 mM.]

[12. The process according to claim 10 wherein potassium chloride is added at a concentration between 8 and 12 mM.]

*13. A serum-free and protein-free cell culture medium for expressing recombinant polypeptides from Chinese Hamster Ovary, Human Embryonic Kidney or SP2/0 myeloma cells having a molar ratio of sodium to potassium ions of between 9 to 1 and 5 to 1.*

*14. A serum-free and protein-free cell culture medium for expressing recombinant polypeptides from Chinese Hamster Ovary, Human Embryonic Kidney or SP2/0 myeloma cells, having sodium ions at a concentration of between 50 and 90 mM and potassium ions at a concentration of between 8 and 12 mM.*

*15. The cell culture medium of claim 13, wherein the sodium ions have a concentration of between 50 and 90 mM.*

*16. The cell culture medium of claim 13 or 14, wherein the sodium ions have a concentration of between 65 and 85 mM.*

*17. The cell culture medium of claim 13, wherein the potassium ions have a concentration of between 8 and 12 mM.*

*18. The cell culture medium of claim 14, wherein the molar ratio of sodium to potassium ions is between 9 to 1 and 5 to 1.*

*19. The cell culture medium of claim 13 or 14 comprising a total amino acid concentration between 40 and 100 mM.*

*20. The cell culture medium of claim 13 or 14, wherein the molar ratio between the total ion concentration to the total amino acid concentration is between 1.9 and 4.*

*21. A process for the production of a recombinant polypeptide comprising culturing mammalian cells comprising a recombinant nucleic acid encoding the recombinant polypeptide in the medium of claim 13 or 14 and expressing the recombinant polypeptide, wherein the mammalian cells are selected from the group consisting of Chinese Hamster Ovary (CHO) cells, Human Embryonic Kidney (HEK) cells, and SP2/0 cells.*

*22. A process for the production of a recombinant polypeptide comprising:*

*(a) culturing mammalian cells comprising a recombinant nucleic acid encoding the recombinant polypeptide in a serum-free and protein-free cell culture medium having a molar ratio of sodium to potassium ions of between 9 to 1 and 5 to 1; and*

*(b) expressing the recombinant polypeptide,*

*wherein the mammalian cells are selected from the group consisting of Chinese Hamster Ovary (CHO) cells, Human Embryonic Kidney (HEK) cells, and SP2/0 cells.*

*23. A process for the production of a recombinant polypeptide comprising:*

*(a) culturing mammalian cells comprising a recombinant nucleic acid encoding the recombinant polypeptide in a serum-free and protein-free cell culture medium having sodium ions at a concentration of between 50 and 90 mM and potassium ions at a concentration of between 8 and 12 mM; and*

*(b) expressing the recombinant polypeptide,*

*wherein the mammalian cells are selected from the group consisting of Chinese Hamster Ovary (CHO) cells, Human Embryonic Kidney (HEK) cells, and SP2/0 cells.*

*24. The process of claim 22, wherein the sodium ions have a concentration of between 50 and 90 mM.*

*25. The process of claim 22 or 23, wherein the sodium ions have a concentration of between 65 and 85 mM.*

*26. The process of claim 22, wherein the potassium ions have a concentration of between 8 and 12 mM.*

*27. The process of claim 23, wherein the molar ratio of sodium to potassium ions is between 9 to 1 and 5 to 1.*

*28. The process of claim 22 or 23, wherein the cultivation of the cells is carried out in adherent culture.*

*29. The process of claim 22 or 23, wherein the cultivation of the cells is carried out in suspension culture.*

*30. The process according to claim 22 or 23, wherein culturing conditions comprise at least one temperature shift and/or at least one pH shift.*

*31. The process according to claim 22 or 23 wherein culturing is done by a fed batch process.*

*32. The process according to claim 22 or 23, wherein the expressed recombinant polypeptide is glycosylated.*

*33. The process according to claim 22 or 23, wherein the expressed polypeptide is an antibody or antibody fragment.*

*34. A process for the production of a cell culture medium according to claim 13 or 14, wherein the medium's components are admixed with each other.*

*35. The process according to claim 22 or 23, wherein sodium chloride is added at a concentration of between 7 and 15 mM.*

*36. The process according to claim 22, wherein the sodium ions are added at a concentration of between 50 and 90 mM.*

*37. The process according to claim 22, wherein the potassium ions are added at a concentration of between 8 and 12 mM.*

*38. The process according to claim 22 or 23, wherein the cell culture medium comprises a total amino acid concentration between 40 and 100 mM.*

*39. The process according to claim 22 or 23, wherein the molar ratio between the total ion concentration to the total amino acid concentration is between 1.9 and 4.*

* * * * *